(12) United States Patent
Lambert et al.

(10) Patent No.: US 9,351,923 B2
(45) Date of Patent: May 31, 2016

(54) EXTENDED-RELEASE COMPOSITION COMPRISING A SOMATOSTATIN DERIVATIVE IN MICROPARTICLES

(71) Applicant: NOVARTIS AG, Basel (CH)

(72) Inventors: Olivier Lambert, Spechbach le Haut (FR); Marc Riemenschnitter, Freiburg (DE); Vitomir Vucenovic, Loerrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/743,385

(22) Filed: Jan. 17, 2013

(65) Prior Publication Data

US 2013/0129798 A1     May 23, 2013

Related U.S. Application Data

(63) Continuation of application No. 12/600,740, filed as application No. PCT/EP2008/056347 on May 23, 2008, now abandoned.

(30) Foreign Application Priority Data

May 24, 2007    (EP) .................................... 07108796

(51) Int. Cl.
| | |
|---|---|
| *A61K 9/00* | (2006.01) |
| *A61K 31/085* | (2006.01) |
| *A61K 9/52* | (2006.01) |
| *A61K 9/50* | (2006.01) |
| *A61K 38/31* | (2006.01) |

(52) U.S. Cl.
CPC ............. *A61K 9/0002* (2013.01); *A61K 9/5031* (2013.01); *A61K 38/31* (2013.01)

(58) Field of Classification Search
CPC ..... A61K 31/085; A61K 9/145; A61K 38/31; A61K 9/0002; A61K 9/146
USPC ........... 424/486, 499, 501; 514/11.1; 530/317
See application file for complete search history.

(56) References Cited

U.S. PATENT DOCUMENTS

| | | | |
|---|---|---|---|
| 5,538,739 | A | 7/1996 | Bodmer et al. |
| 5,876,761 | A | 3/1999 | Bodmer |
| 2005/0074492 | A1 | 4/2005 | Ignatious |
| 2006/0121120 | A1 | 6/2006 | Ignatious |

FOREIGN PATENT DOCUMENTS

| | | |
|---|---|---|
| CA | 2316052 A1 | 1/1991 |
| EP | 1240896 A2 | 9/2002 |
| WO | 98/32423 A1 | 7/1998 |
| WO | 2005/046645 | 5/2005 |
| WO | 2005/053732 A1 | 6/2005 |

OTHER PUBLICATIONS

Spectrum (MSDS for Resomer RG 502H, http://wcam.engr.wisc.edu/Public/Safety/MSDS/Poly%20(DL-Lactide-CO-Glycolide)%20.pdf, accessed May 3, 2015).*
Blanco-Prietro, M.J. et al., "Importance of single or blended polymer types for controlled in vitro release and plasma levels of a somatostatin analogue entrapped in PLA/PLGA microspheres", Journal of Controlled Release, Elsevier, Amsterdam, NL, vol. 96, No. 3, pp. 437-448, (May 18, 2004).

* cited by examiner

*Primary Examiner* — Alma Pipic
(74) *Attorney, Agent, or Firm* — Michelle Han

(57) ABSTRACT

The present invention relates to improved microparticles comprising a somatostatin analog, a process of making said microparticles and to pharmaceutical compositions comprising the same.

2 Claims, 1 Drawing Sheet

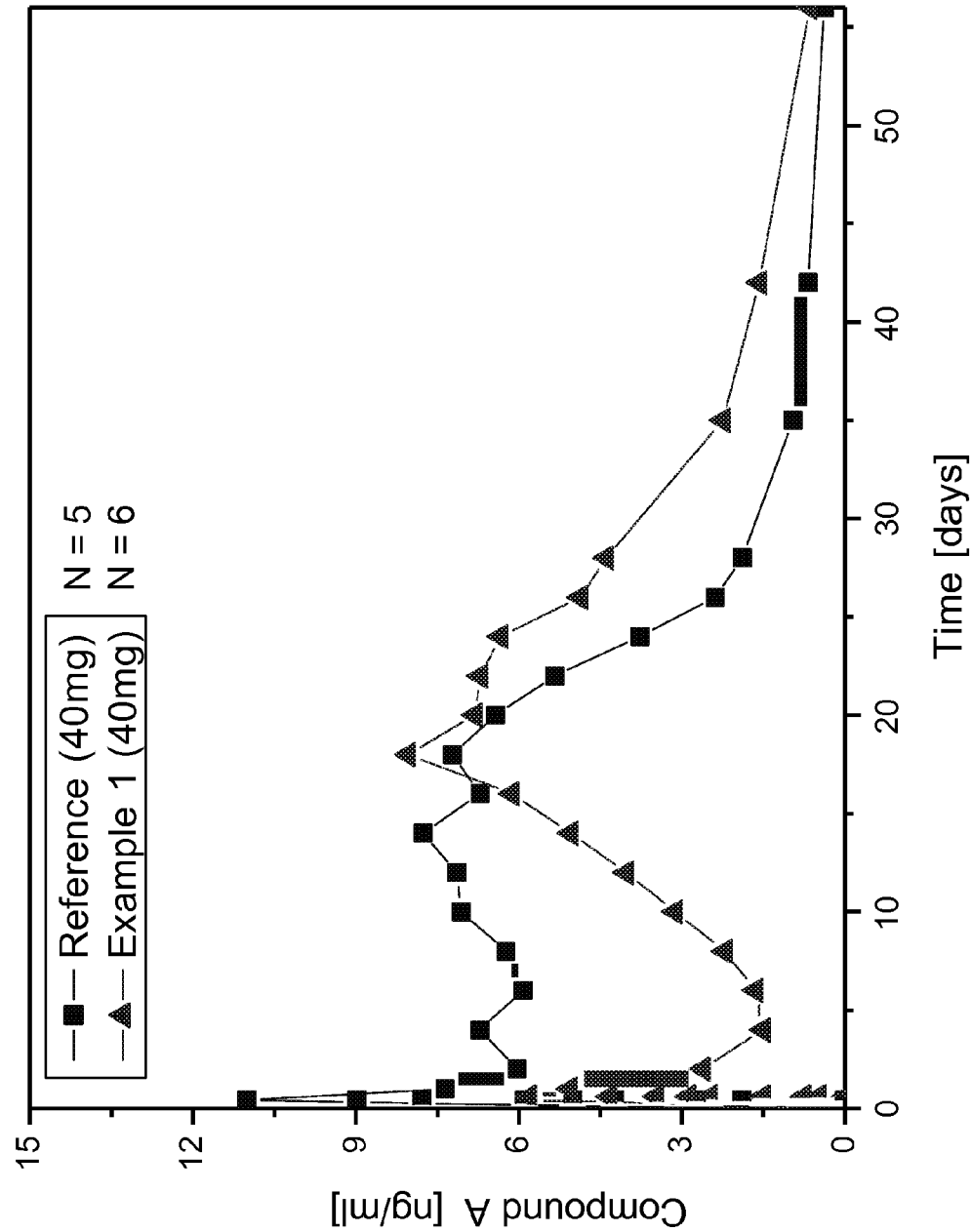

EXTENDED-RELEASE COMPOSITION COMPRISING A SOMATOSTATIN DERIVATIVE IN MICROPARTICLES

The present invention relates to improved microparticles comprising a somatostatin analogue, a process of making said microparticles and to pharmaceutical compositions comprising the same.

The preferred somatostatin analogue according to the present invention is Compound A of formula

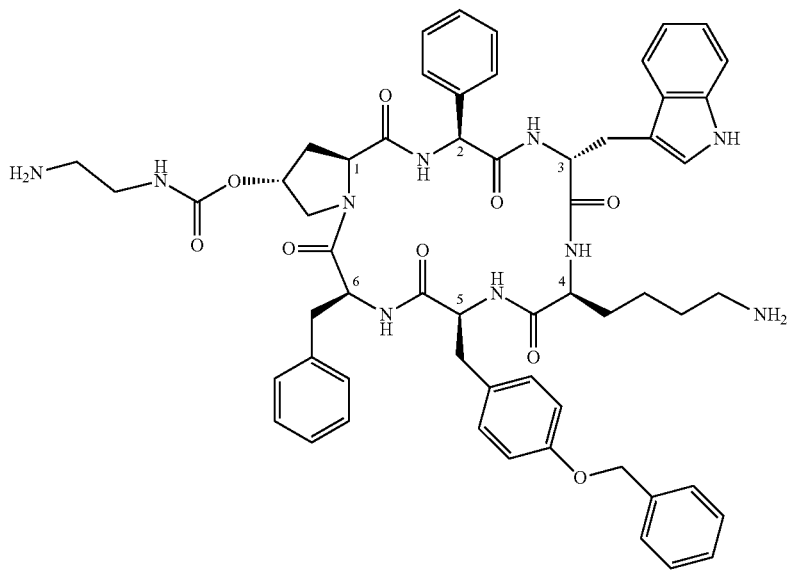 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O]

also called cyclo[{4-($NH_2$—$C_2H_4$—NH—CO—O—)Pro}-Phg-DTrp-Lys-Tyr(4-Bzl)-Phe] or pasireotide, as well as diastereoisomers and mixtures thereof, in free form, in salt or complex form or in protected form. Phg means —HN—CH($C_6H_5$)—CO— and Bzl means benzyl.

Preferred salts for Compound A are the lactate, aspartate, benzoate, succinate and pamoate including mono- and di-salts, more preferably the aspartate di-salt and the pamoate monosalt, most preferred the pamoate monosalt.

The compounds of the invention, including its salts, may be prepared in accordance with conventional methods. Compound A and its synthesis have been described in detail e.g. in WO02/10192, the contents of which are incorporated herein by reference.

WO05/046645, the contents of which are incorporated herein by reference, describes that administration of microparticles comprising a somatostatin analogue, for instance Compound A, e.g. embedded in a biocompatible pharmacologically acceptable polymer, suspended in a suitable vehicle gives release of all or of substantially all of the active agent over an extended period of time, e.g. several weeks up to 6 months, preferably over at least 4 weeks.

However, the microparticle formulations of Compound A as described in WO05/046645 have sometimes a less favourable pharmakokinetic release profile of the active ingredient (drug). The duration of action sometimes is unsatisfactory, i.e. not long lasting enough.

However, especially the relatively high initial release of the drug within the first day(s) after administration (drug burst) can lead to problems, such as for instance unwanted side effects including e.g. nausea or temporarily too high blood glucose level. This drug burst is even more concerning at repeated dosing when the plasma concentration of the drug reaches steady state conditions at higher levels.

Surprisingly, it has been found that keeping the overall composition of the formulation constant but changing the polymer/drug concentration during the process of making the microparticles comprising Compound A results in microparticles with improved properties.

Pharmaceutical compositions comprising the new microparticels according to the present invention show a lower initial release of the active ingredient and/or a longer duration of action and/or a favourable pharmacokinetic release profile, especially at repeated dosing, compared to pharmaceutical compositions comprising the microparticles described in WO05/046645.

The improved properties of pharmaceutical compositions according to the present invention can, for instance, be documented by results obtained in clinical studies in humans.

FIG. 1 shows comparative release profiles of Compound A in healthy human volunteers following a single dose administration of 40 mg Compound A in microparticles either according to Example 1 or according to Reference example (Example 8 of WO05/046645). The microparticles were suspended in vehicle D and administered intramuscular (i.m.). Blood samples were taken periodically and plasma levels of Compound A were measured by Radioimmunoassay (RIA) analysis. The obtained results show a significantly reduced drug burst in the release profile of microparticles according to the present invention compared to the pharmakokinetic profile of microparticles according to the reference example.

The improved properties of pharmaceutical compositions according to the present invention can, for instance, also be determined by in vivo experiments in rabbits. The results obtained in rabbits can easily and reliably be transferred to the corresponding situation in humans, because the pharmacological profile in rabbits and humans with regard to Compound A are closely related.

The release profile of the pharmaceutical compositions according to the present invention after single administration in rabbits can be summarized as follows:

In one embodiment the present invention provides a pharmaceutical composition for extended release comprising microparticles with a polymer matrix comprising one or more biodegradable polymers and Compound A pamoate as active ingredient wherein the maximum plasma concentration (burst) of the active ingredient in rabbits within the first 24 hours after administration of 4 mg/kg is below 15, preferably 12 or 10 ng/ml.

In a preferred embodiment of the present invention, the pharmaceutical compositions for extended release of the present invention comprises microparticles with a polymer matrix consisting of one or more biodegradable polymers and Compound A pamoate as active ingredient.

In another embodiment the present invention provides a pharmaceutical composition for extended release comprising microparticles with a polymer matrix comprising one or more biodegradable polymers and Compound A pamoate as active ingredient wherein in rabbits the ratio of the maximum plasma concentration (burst) of the active ingredient within the first 24 hours after administration and the minimum plasma concentration of the active ingredient between day 2 and 10 after administration is less than 5 or less than 4. Even more preferred is a ratio of the maximum plasma concentration (burst) of the active ingredient within the first 24 hours after administration and the minimum plasma concentration of the active ingredient between day 2 and 10 after administration of less than 3.7 or, preferably, less than 3.6.

In another embodiment the present invention provides a pharmaceutical composition for extended release comprising microparticles with a polymer matrix comprising one or more biodegradable polymers and Compound A pamoate as active ingredient wherein in rabbits the maximum plasma concentration ($t_{max}$) of Compound A is reached not before day 12 after administration.

In another embodiment the present invention provides a pharmaceutical composition for extended release comprising microparticles with a polymer matrix comprising one or more biodegradable polymers and Compound A pamoate as active ingredient wherein in rabbits the plasma concentration of Compound A is above 2 ng/ml between day 2 and day 35 after administration.

In another embodiment the present invention provides a pharmaceutical composition for extended release comprising microparticles with a polymer matrix comprising one or more biodegradable polymers and Compound A pamoate as active ingredient wherein the active ingredient Compound A is released over a time period of at least 4 weeks.

In another embodiment the present invention provides also a pharmaceutical depot formulation comprising the microparticles of the present invention.

The burst release of Compound A can alternatively, or additionally, be measured by an in vitro dissolution test, e.g., as described in Example 4 of the present application. In one embodiment, the present invention provides a pharmaceutical composition for extended release comprising microparticles with a polymer matrix comprising one or more biodegradable polymers and Compound A pamoate as active ingredient wherein the burst measured as % of Compound A content after 24 hours is less than 1.2%, less than 1.0%, less than 0.9% or less than 0.8%. The burst measured by the dissolution test as % of Compound A content after 24 hours is conveniently between 0.5% to 1.2% or 0.6% to 1.0%.

In another embodiment the present invention provides a method of treatment of a disease amenable to treatment with Compound A in a patient in need of such treatment comprising administering to the patient a dosage form for parenteral administration of Compound A pamoate, said dosage form comprising microparticles as described herein, wherein said dosage form releases Compound A in rabbits such that a maximum plasma concentration (burst) of the active ingredient in rabbits within the first 24 hours after administration of 4 mg/kg is below 15, preferably 12 or 10 ng/ml. In one embodiment of the method the maximum plasma concentration ($t_{max}$) of Compound A in rabbits is reached not before day 12 after administration. In another embodiment, the plasma concentration of Compound A in rabbits is above 2 ng/ml between day 2 and day 35. Alternatively or additionally, the burst release is measured with the method as described in Example 4 and is less than 1.2% or 1% of Compound A content. The administration can for instance be done at least every 2 weeks or at least every 4 weeks (including e.g. monthly) or at least every 6 weeks or at least every 8 weeks (or e.g. every two months). Diseases amenable to Compound A include diseases or disorders with an aetiology comprising or associated with excess GH- and/or IGF-1 secretion.

In one embodiment the present invention provides the use of a formulation of compound Compound A obtainable by a process for the preparation of microparticles as described hereinbelow in the manufacture of a medicament for the treatment of disorders with an aetiology comprising or associated with excess GH-secretion and/or excess of IGF-1.

In another embodiment the present invention provides the use of Compound A in the manufacture of a medicament for treating a disease amenable to treatment with Compound A wherein Compound A is in a dosage form for parenteral administration comprising microparticles with a polymer matrix comprising one or more biodegradable polymers and Compound A pamoate as active ingredient characterized in that the microparticles release compound A in rabbits is such that a maximum plasma concentration (burst) of the active ingredient in rabbits within the first 24 hours after administration of 4 mg/kg is below 15, preferably 12 or 10 ng/ml. In one embodiment, the maximum plasma concentration ($t_{max}$) of Compound A in rabbits is reached not before day 12 after administration. In another embodiment, the plasma concentration of Compound A in rabbits is above 2 ng/ml between day 2 and day 35. The burst release may alternatively or additionally be measured by the dissolution test as described in Example 4 and is less than 1.2% or 1% of Compound A content.

In another embodiment the present invention provides the use of a pharmaceutical composition for extended release comprising microparticles with a polymer matrix comprising of one or more biodegradable polymers, e.g. a mixture of a linear polylactide-co-glycolide polymer and a branched polylactide-co-glycolide polymer, and Compound A pamoate as active ingredient, wherein the microparticles have been prepared by a process for preparing microparticles as described hereinbelow characterized in that methylene chloride in a concentration from 14.24% to 17.45%, preferably from 15.0% to 16.5%, even more preferred about 15.9% (weight/weight) is used to dissolve the polymer mixture. Such pharmaceutical compositions can for instance be used in the manufacture of a medicament for the treatment of Acromegaly, GEP tumors, Cushing and Tumors such as e.g. Hepatocellular carcinoma, breast cancer. Such compositions have an advantageous release profile for Compound A and in particular a reduced initial burst, as described in the present application.

Compound A (free base) may be present in an amount of from about 1 to about 35%, preferably from about 10 to about 35%, even more preferably from about 20% to about 30%, by weight of the microparticles dry weight.

Preferably, the compound of the invention used to prepare the microparticles is in the form of an amorphous powder.

The particle size and/or the particle size distribution of the compound of the invention may influence the release profile of the drug from the microparticles.

Typically, the smaller the particle size, the lower is the burst and the release during the first diffusion phase, e.g. the first 20 days. Preferably, the particles of the compound of the invention used to prepare the microparticles have a size of about 0.1 microns to about 15 microns, preferably less than about 5 microns, even more preferably less than about 3 microns.

The particle size distribution is preferably ×10<0.8 microns, i.e. 10% of the particles are smaller than 0.8 microns; ×50<3.0 microns i.e. 50% of the particles are smaller than 3.0 microns; or ×90<5.0 microns, i.e. 90% of the particles are smaller than 5.0 microns.

The polymer matrix of the microparticles comprises of one or more biodegradable polymers. By "polymer" is meant an homopolymer or a copolymer. In a preferred embodiment, the polymer matrix of the microparticles consist of one or more biodegradable polymers.

The polymer matrix is designed to degrade sufficiently to be transported from the site of administration within one to 6 months after release of all or substantially all the active agent.

The preferred polymers of this invention are linear polyesters and branched chain polyesters (i.e. polyesters which have linear chains radiating from a polyol moiety, e.g. glucose). The linear polyesters may be prepared from α-hydroxy carboxylic acids, e.g. lactic acid and/or glycolic acid, by condensation of the lactone dimers, see e.g. U.S. Pat. No. 3,773, 919, the contents of which are incorporated herein by reference.

The preferred polyester chains in the linear or branched (star) polymers are copolymers of the α-carboxylic acid moieties, lactic acid and glycolic acid, or of the lactone dimers. The molar ratio of lactide:glycolide of polylactide-co-glycolides in the linear or branched polyesters is preferably from about 75:25 to 25:75, e.g. 60:40 to 40:60, with from 55:45 to 45:55, e.g. 52:48 to 48:52 the most preferred. Particularly preferred is about 50:50.

Linear polyesters, e.g. linear polylactide-co-glycolides (PLG), preferably used according to the invention have a weight average molecular weight (Mw) between about 10,000 and about 500,000 Da, e.g. between about 47,000 to about 63,000, e.g. about 50,000 Da. Such polymers have a polydispersity $M_w/M_n$ e.g. between 1.2 and 2. Suitable examples include e.g. poly(D,L-lactide-co-glycolide), e.g. having a general formula —[($C_6H_8O_4$)$_x$($C_4H_4O_4$)$_y$]$_n$— (each of x, y and n having a value so that the total sum gives the above indicated Mws), e.g. those commercially available, e.g. Resomers® from Boehringer Ingelheim, in particular Resomers® RG, e.g. Resomer® RG 502, 502H, 503, 503H, 504, 504H.

Branched polyesters, e.g. branched polylactide-co-glycolides, preferably used according to the invention may be prepared using polyhydroxy compounds e.g. polyol e.g. glucose or mannitol as the initiator. These esters of a polyol are known and described e.g. in GB 2,145,422 B, the contents of which are incorporated herein by reference. The polyol contains at least 3 hydroxy groups and has a molecular weight of up to 20,000 Da, with at least 1, preferably at least 2, e.g. as a mean 3 of the hydroxy groups of the polyol being in the form of ester groups, which contain poly-lactide or co-poly-lactide chains. Typically 0.2% glucose is used to initiate polymerization. The branched polyesters (Glu-PLG) have a central glucose moiety having rays of linear polylactide chains, e.g. they have a star shaped structure.

The branched polyesters having a central glucose moiety having rays of linear polylactide-co-glycolide chains (Glu-PLG) may be prepared by reacting a polyol with a lactide and preferably also a glycolide at an elevated temperature in the presence of a catalyst, which makes a ring opening polymerization feasible.

The branched polyesters having a central glucose moiety having rays of linear polylactide-co-glycolide chains (Glu-PLG) preferably have an weight average molecular weight $M_w$ in the range of from about 10,000 to 200,000, preferably 25,000 to 100,000, especially 35,000 to 60,000 or 47,000 to 63,000, e.g. about 50,000 Da, and a polydispersity e.g. of from 1.5 to 3.0, e.g. 1.7 to 2.5. The intrinsic viscosities of star polymers of $M_w$ 35,000 or $M_w$ 60,000 are from 0.20 dl/g to 0.70 dl/g, such as e.g. 0.36 or 0.51 dl/g, respectively, in acetone or chloroform. A star polymer having a $M_w$ 53,800 has a viscosity of 0.25 dl/g to 0.50 dl/g in acetone or chloroform such as e.g. 0.34 dl/g in acetone at room temperature.

Preferably, the polymer matrix comprises a linear and a branched polylactide-co-glycolide. More preferably, the polymer matrix comprises a Resomer® RG and a star polylactide-co-glycolide polymer having a weight average molecular weight of between about 47,000 to about 63,000, e.g. about 50,000 Da. The ratio of linear to branched polylactide-co-glycolide preferably is 50:50 to 25:75. More preferably the ratio is about 50:50.

The polymer matrix may be present in a total amount of about 40 to 99% by weight of the microparticles.

The present invention in another embodiment provides a process for the preparation of microparticles of the invention comprising
(i) preparation of an internal organic phase comprising
  (ia) dissolving the polymers in methylene cloride in a concentration from 14.24% to 17.45%, preferably from 15.0% to 16.5%, even more preferred about 15.9% (weight/weight)
  and optionally
    dissolving/dispersing a porosity-influencing agent in the solution obtained in step (ia), or
    adding a basic salt to the solution obtained in step (ia), adding a surfactant to the solution obtained by step (ia);
  (ib) suspending the compound of the invention in the polymer solution obtained in step (ia), or
    dissolving the compound of the invention in a solvent miscible with the solvent used in step (ia) and mixing said solution with the polymer solution, or
    directly dissolving the compound of the invention in the polymer solution, or
    dissolving the compound of the invention in form of a water soluble salt in an aqueous phase and emulsifying said aqueous solution with the polymer solution (ia);
(ii) preparation of an external aqueous phase comprising
  (iia) preparing a buffer to adjust the pH to 7-7.5, e.g. acetate or phosphate buffer, e.g. $Na_2HPO_4$ and $KH_2PO_4$, and
  (iib) dissolving a stabilizer in the solution obtained in step (iia);
(iii) mixing the internal organic phase with the external aqueous phase e.g. with a device creating high shear forces, e.g. with a turbine or static mixer, or by applying ultrasound or by ultrasonic homogenization to form an emulsion; and
(iv) hardening the microparticles by solvent evaporation or solvent extraction, washing the microparticles, e.g. with water, collecting and drying the microparticles, e.g. freeze-drying or drying under vacuum.

Suitable organic solvents for the polymers include halogenated hydrocarbons, e.g. methylene chloride, chloroform or hexafluoroisopropanol or ethyl acetate. The preferred organic solvent is methylene chloride. The concentration of the polymer mixture in methylene chloride is between 14.24% and 17.45% (weight polymer per weight polymer solution), preferably from 15.0% to 16.5%, even more preferred about 15.9% (weight/weight).

Suitable examples of a stabilizer for step (iib) include
a) Polyvinyl alcohol (PVA), preferably having a weight average molecular weight from about 10,000 to about 150,000 Da, e.g. about 30,000 Da. Conveniently the polyvinyl alcohol has low viscosity having a dynamic viscosity of from about 3 to about 9 mPa s when measured as a 4% aqueous solution at 20° C. or by DIN 53015. Suitably the polyvinyl alcohol may be obtained from hydrolyzing polyvinyl acetate. Preferably, the content of the polyvinyl acetate is from about 10 to about 90% of the polyvinyl alcohol. Conveniently the degree of hydrolysis is about 85 to about 89%. Typically the residual acetyl content is about 10 to 12%. Preferred brands include Mowiol® 4-88, 8-88 and 18-88 available from Clariant AG Switzerland.

Preferably the polyvinyl alcohol is present in an amount of from about 0.1 to about 5%, e.g. about 0.5%, by weight of the volume of the external aqueous phase;

b) Hydroxyethyl cellulose (HEC) and/or hydroxypropyl cellulose (HPC), e.g. formed by reaction of cellulose with ethylene oxide and propylene oxide respectively. HEC and HPC are available in a wide range of viscosity types; preferably the viscosity is medium. Preferred brands include Natrosol® from Hercules Inc., e.g. Natrosol® 250MR, and Klucel® from Hercules Inc.

Preferably, HEC and/or HPC is present in a total amount of from about 0.01 to about 5%, e.g. about 0.5%, by weight of the volume of the external aqueous phase;

c) Polyvinylpyrolidone, e.g. suitably with a molecular weight of between about 2,000 and 20,000 Da. Suitable examples include those commonly known as Povidone K12 F with an average molecular weight of about 2,500 Da, Povidone K15 with an average molecular weight of about 8,000 Da, or Povidone K17 with an average molecular weight of about 10,000 Da. Preferably, the polyvinylpyrrolidone is present in an amount of from about 0.1 to about 50%, e.g. 10% by weight of the volume of the external aqueous phase;

d) Gelatin, preferably porcine or fish gelatin. Conveniently, the gelatin has a viscosity of about 25 to about 35 cps for a 10% solution at 20° C. Typically pH of a 10% solution is from about 6 to about 7. A suitable brand has a high molecular weight, e.g. Norland high molecular weight fish gelatin obtainable from Norland Products Inc, Cranbury N.J. USA.

Preferably, the gelatin is present in an amount of from about 0.01 to about 5%, e.g. about 0.5%, by weight of the volume of the external aqueous phase.

Preferably, polyvinyl alcohol or gelatine is used. Most preferred is polyvinyl alcohol, especially PVA 18-88.

In a preferred embodiment the process of making microparticles comprises the steps of
dissolving a mixture of a linear polylactide-co-glycolide polymer and a branched polylactide-co-glycolide polymer in methylene chloride,
adding this polymer solution to the active ingredient Compound A pamoate,
preparing an aqueous solution of phosphate salts and polyvinyl alcohol
mixing the polymer/active ingredient solution with the polyvinyl alcohol/phosphate solution,
evaporating the methylene chloride and filtering off the obtained microparticles,
wherein the concentration of the polymer mixture in methylene chloride is between 14.2% and 17.5% weight by weight.

Even more preferred is a concentration of the polymer mixture in methylene chloride of about 15.9% weight by weight.

The resulting microparticles may have a diameter from a few submicrons to a few millimeters; e.g. diameters of at most about 250 microns, e.g. 10 to 200 microns, preferably 10 to 130 microns, more preferably 10 to 90 microns, even more preferably 10 to 60 microns, are strived for, e.g. in order to facilitate passage through an injection needle. A narrow particle size distribution is preferred. For example, the preferred particle size distribution is x10<15 microns, x50<40 microns and x90<70 microns.

Content uniformity of the microparticles and of a unit dose is excellent. Unit doses may be produced which vary from about 75% to about 125%, e.g. about 85% to about 115%, e.g. from about 90% to about 110%, or from about 95% to about 105%, of the theoretical dose.

The microparticles in dry state may e.g. be mixed, e.g. coated, with an anti-agglomerating agent, or e.g. covered by a layer of an anti-agglomerating agent e.g. in a prefilled syringe or vial.

Suitable anti-agglomerating agents include e.g. mannitol, glucose, dextrose, sucrose, sodium chloride, or water soluble polymers such as polyvinylpyrrolidone or polyethylene glycol, e.g. with the properties described above.

Preferably, an anti-agglomerating agent is present in an amount of about 0.1 to about 10%, e.g. about 4% by weight of the microparticles.

Prior to administration, the microparticles are suspended in a vehicle suitable for injection.

Accordingly, the present invention further provides a pharmaceutical composition comprising microparticles of the invention in a vehicle. The vehicle may optionally further contain: a) one or more wetting agents; and/or b) one or more tonicity agent; and/or c) one or more viscosity increasing agents.

Preferably, the vehicle is water based, e.g. it may contain water, e.g deionized, and optionally a buffer to adjust the pH to 7-7.5, e.g. a phosphate buffer such as a mixture of $Na_2HPO_4$ and $KH_2PO_4$, and one or more of agents a), b) and/or c) as indicated above.

However, when using water as a vehicle, the microparticles of the invention may not suspend and may float on the top of the aqueous phase. In order to improve the capacity of the microparticles of the invention to be suspended in an aqueous medium, the vehicle preferably comprises a wetting agent a). The wetting agent is chosen to allow a quick and suitable suspendibility of the microparticles in the vehicle. Preferably, the microparticles are quickly wettened by the vehicle and quickly form a suspension therein.

Suitable wetting agents for suspending the microparticles of the invention in a water-based vehicle include non-ionic surfactants such as poloxamers, or polyoxyethylene-sorbitan-fatty acid esters, the characteristics of which have been described above. A mixture of wetting agents may be used. Preferably, the wetting agent comprises Pluronic F68, Tween 20 and/or Tween 80.

The wetting agent or agents may be present in about 0.01 to about 1% by weight of the composition to be administered, preferably from 0.01 to 0.5% and may be present in about 0.01 to 5 mg/ml of the vehicle, e.g. about 2 mg/ml.

Preferably, the vehicle further comprises a tonicity agent b) such as mannitol, sodium chloride, glucose, dextrose, sucrose, or glycerin. Preferably, the tonicity agent is mannitol.

The amount of tonicity agent is chosen to adjust the isotonicity of the composition to be administered. In case a tonicity agent is contained in the microparticles, e.g. to reduce agglomeration as mentioned above, the amount of tonicity agent is to be understood as the sum of both. For example, mannitol preferably may be from about 1% to about 5% by weight of the composition to be administered, preferably about 4.5%.

Preferably, the vehicle further comprises a viscosity increasing agent c). Suitable viscosity increasing agents include carboxymethyl cellulose sodium (CMC-Na), sorbitol, polyvinylpyrrolidone, or aluminium monostearate.

CMC-Na with a low viscosity may conveniently be used. Embodiments may be as described above. Typically, a CMC-Na with a low molecular weight is used. The viscosity may be of from about 1 to about 30 mPa s, e.g. from about 10 to about 15 mPa s when measured as a 1% (w/v) aqueous solution at 25° C. in a Brookfield LVT viscometer with a spindle 1 at 60 rpm, or a viscosity of 1 to 15 mPa*s for a solution of NaCMC 7LF (low molecular weight) as a 0.1 to 1% solution in water.

A polyvinylpyrrolidone having properties as described above may be used.

A viscosity increasing agent, e.g. CMC-Na, may be present in an amount of from about 0.1 to about 2%, e.g. about 0.7% or about 1.75% of the vehicle (by volume), e.g. in a concentration of about 1 to about 30 mg/ml in the vehicle, e.g. about 7 mg/ml or about 17.5 mg/ml.

In a further aspect, the present invention provides a kit comprising microparticles of the invention and a vehicle of the invention. For example, the kit may comprise microparticles comprising the exact amount of compound of the invention to be administered, e.g. as described below, and about 1 to about 5 ml, e.g. about 2 ml of the vehicle of the invention.

In one embodiment, the dry microparticles, optionally in admixture with an anti-agglomerating agent, may be filled into a container, e.g. a vial or a syringe, and sterilized e.g. using γ-irradition. Prior to administration, the microparticles may be suspended in the container by adding a suitable vehicle, e.g. the vehicle described above. For example, the microparticles, optionally in admixture with an anti-agglomerating agent, a viscosity increasing agent and/or a tonicity agent, and the vehicle for suspension may be housed separately in a double chamber syringe. A mixture of the microparticles with an anti-agglomerating agent and/or a viscosity increasing agent and/or a tonicity agent, also forms part of the invention.

In another embodiment, under sterile conditions dry sterilized microparticles, optionally in admixture with an anti-agglomerating agent, may be suspended in a suitable vehicle, e.g. the vehicle described above, and filled into a container, e.g. a vial or a syringe. The solvent of the vehicle, e.g. the water, may then be removed, e.g. by freeze-drying or evaporation under vacuum, leading to a mixture of the microparticles and the solid components of the vehicle in the container. Prior to administration, the microparticles and solid components of the vehicle may be suspended in the container by adding a suitable vehicle, e.g. water, e.g. water for infusion, or preferably a low molarity phosphate buffer solution. For example, the mixture of the microparticles, optionally the anti-agglomerating agent, and solid components of the vehicle and the vehicle for suspension, e.g. water, may be housed separately in a double chamber syringe.

The microparticles and the compositions of the invention are useful a) for the prevention or treatment of disorders with an aetiology comprising or associated with excess GH-secretion and/or excess of IGF-1 e.g. in the treatment of acromegaly as well as in the treatment of type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity, b) in the treatment of enterocutaneous and pancreaticocutaneous fistula, irritable bowel syndrom, inflammatory diseases, e.g. Grave's Disease, inflammatory bowel disease, psoriasis or rheumatoid arthritis, polycystic kidney disease, dumping syndrom, watery diarrhea syndrom, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g variceal oesophagial bleeding, c) for the prevention or treatment of angiogenesis, inflammatory disorders as indicated above including inflammatory eye diseases, macular edema, e.g. cystoid macular edema, idiopathic cystoid macular edema, exudative age-related macular degeneration, choroidal neovascularization related disorders and proliferative retinopathy, d) for preventing or combating graft vessel diseases, e.g. allo- or xenotransplant vasculo-pathies, e.g. graft vessel atherosclerosis, e.g. in a transplant of organ, e.g. heart, lung, combined heart-lung, liver, kidney or pancreatic transplants, or for preventing or treating vein graft stenosis, restenosis and/or vascular occlusion following vascular injury, e.g. caused by catherization procedures or vascular scraping procedures such as percutaneous transluminal angioplasty, laser treatment or other invasive procedures which disrupt the integrity of the vascular intima or endothelium, e) for treating somatostatin receptor expressing or accumulating tumors such as pituitary tumors, e.g. Cushing's Disease or Syndrome, gastro-enteropancreatic, carcinoids, central nervous system, breast, prostatic (including advanced hormone-refractory prostate cancer), ovarian or colonic tumors, small cell lung cancer, malignant bowel obstruction, paragangliomas, kidney cancer, skin cancer, neuroblastomas, pheochromocytomas, medullary thyroid carcinomas, myelomas, lymphomas, Hodgkins and non-Hodgkins lymphomas, bone tumours and metastases thereof, as well as autoimmune or inflammatory disorders, e.g. rheumatoid arthritis, Graves disease or other inflammatory eye diseases.

Preferably, the microparticles and the compositions of the invention are useful in the treatment of acromegaly and cancer, e.g. Cushing's Disease or Syndrome, carcinoids.

The properties of the microparticles and the compositions of the invention may be tested in standard animal tests or clinical trials.

The microparticles and the compositions of the invention are well-tolerated.

The compounds of the invention are released from the microparticles of the invention and from the compositions of the invention over a period of several weeks e.g. about 4 weeks to about 8 weeks, preferably about 4 weeks to about 6 weeks.

Appropriate dosage of the composition of the invention will of course vary, e.g. depending on the condition to be treated (for example the disease type or the nature of resistance), the drug used, the effect desired and the mode of administration.

In general, satisfactory results are obtained on administration, e.g. parenteral administration, at dosages on the order of from about 0.2 to about 100 mg, e.g. 0.2 to about 35 mg, preferably from about 3 to about 100 mg of Compound A per injection per month or about 0.03 to about 1.2 mg, e.g. 0.03 to 0.3 mg per kg body weight per month. Suitable monthly dosages for patients are thus in the order of about 0.3 mg to about 100 mg of Compound A.

The following Examples serve to illustrate the invention, without any limitation:

Example 1

Microparticles

The polymers are dissolved in an amount of methylene chloride as indicated in Table 1. The polymer solution is then added to the Compound A pamoate. The resulting suspension is treated with an Ultra-Turrax for 1 min.

2 l of water are heated to 90° C. During warming, the phosphate salts in an amount as given in Table 1 are added one after another. At 90° C., PVA 18-88 in an amount as given in Table 1 is added. The resulting solution is then cooled to 20° C. and filled up with water to the required volume.

The polymer/drug suspension and the PVA/phosphate solution are mixed at constant pump rates of 90 ml/min and 1800 ml/min at a mixing speed of 3300 upm, methylene chloride is evaporated under vacuum using a temperature program, which heats 2° C. per 20 min over 300 min. Subsequently, the microparticles are filtered off, washed with water (WBU) and dried under reduced pressure (0.1 mbar) at room temperature.

Dried microparticles are filled in vials, evacuated and terminally sterilized. Terminal sterilization is performed by gamma-irradiation applying irradiation dose of 27.7 to 34.1 kGy.

TABLE 1

(Amounts given in g)

| | Example 1 | Reference Example (Ex. 8 of WO05/046645) |
|---|---|---|
| Star polymer: Poly-(D,L-lactide-co-glycolide) with a $M_w$ of about 50,000 Da Molar Ratio lactide:glycolide 50:50 | 1.30 | 1.278 |
| Resomer RG 502H Molar Ratio lactide:glycolide 50:50 | 1.30 | 1.278 |
| Methylene chloride | 13.780 | 16.926 |
| Compound A pamoate | 1.401 | 1.445 |
| Polyvinyl alcohol (PVA) 18-88 | 15.00 | 15.00 |
| $KH_2PO_4$ | 5.43 | 5.43 |
| $Na_2HPO_4$ anhydrous | 22.71 | 22.71 |
| Water (WBU) | Ad 3.0 l | Ad 3.0 l |

Example 2

Vehicle Compositions A to G

CMC-Na, Mannitol and Pluronic F68 in an amount as given in Table 2 are dissolved in about 15 ml hot deionized water of a temperature of about 90° C. under strong stirring with a magnetic stirrer. The resulting clear solution is cooled to 20° C. and filled up with deionized water to 20.0 ml.

TABLE 2

(Amounts given in g)

| | A | B | C | D | E | F | G |
|---|---|---|---|---|---|---|---|
| CMC-Na | 0 | 0 | 0.05 | 0.14 | 0.28 | 0.35 | 0.40 |
| Mannitol | 0 | 1.04 | 0.99 | 0.90 | 0.76 | 0.74 | 0.68 |
| Pluronic F68 | 0.04 | 0.04 | 0.04 | 0.04 | 0.04 | 0.04 | 0.04 |

Vehicle D is preferred for use with microparticles in vials
Vehicle E is preferred for use in double chamber syringe.

Example 3

Release of Compound A from Microparticles

Microparticles of example 1 and of Reference Example in an amount corresponding to 4 mg of Compound A per kg of the rabbit are suspended in 1 ml of the vehicle composition D. The suspension is homogenized by shaking for about 30 seconds and injected into the left Musculus gastronemius of rabbits (Male Chinchilla bastard rabbits, about 7 months old), weighing about 3 kg before onset of the study, using an 19 G needle.

Blood samples (about 1 ml) are collected over 55 days. Plasma levels of Compound A are determined using an ELISA method. Mean concentration of Compound A after administration is given in Table 3. Mean AUC (0-55 d) is found to be 287 ng/ml d for example 1 and 227 ng/ml d for reference example.

TABLE 3

(mean concentration in ng/ml)

| | Time after administration [days] | | | | | | | | | |
|---|---|---|---|---|---|---|---|---|---|---|
| | 0 | 0.021 | 0.042 | 0.083 | 0.167 | 0.25 | 1 | 2 | 3 | 6 | 9 |
| Microparticles of Ex. 1 | 0 | 2.20 | 3.64 | 6.66 | 8.33 | 8.04 | 3.69 | 2.87 | 2.34 | 3.83 | 6.46 |
| Microparticles of Reference Example | 0 | 12.40 | 11.51 | 17.61 | 17.13 | 13.09 | 5.73 | 4.58 | 4.58 | 13.32 | 9.15 |

TABLE 3-continued (mean concentration in ng/ml)

| | Time after administration [days] | | | | | | | | | | |
|---|---|---|---|---|---|---|---|---|---|---|---|
| | 13 | 16 | 20 | 23 | 27 | 30 | 34 | 37 | 41 | 44 | 49 |
| Microparticles of Ex. 1 | 8.30 | 8.95 | 12.50 | 10.31 | 7.46 | 7.76 | 6.45 | 3.20 | 1.03 | 1.01 | 0.53 |
| Microparticles of Reference Example | 4.82 | 4.93 | 6.89 | 6.22 | 7.71 | 3.30 | 1.39 | 0.88 | 0.47 | 0.0 | 0.0 |

Example 4

Burst Release of Compound A from Microparticles

The dissolution tests were performed in shaker bath set at 37° C., 80 min-1 (n=3) for 24 h. The samples were weighted into polyester bags of 4×4 cm and tightly sealed. The sample bags were placed into 50 ml Schott bottles and 50 ml of pre-warmed (37° C.) medium was added.

Medium was prepared by dissolving e.g. 2.98 g di-sodium hydrogen phosphate dihydrate, 8.0 g sodium chloride, 0.19 g potassium dihydrogen phosphate, 0.01 g benzalkonium chloride and 0.2 g tween 80 in 1000 ml of water and adjusting the pH with phosphoric acid 85% to 7.4

After 24 h the medium was aspirated. Data was normalized to the sample weight within the individual bags. The burst can be measured as % Drug Content which is the percentage of drug released related to the before determined assay, i.e. if 100 mg MP contains 25 mg Compound A and 0.25 mg Compound A are released after 24 h this means the burst is 1%.

TABLE 4

(burst as % of drug content)

| Burst | 0 h | 24 h |
|---|---|---|
| Microparticles of Ex. 1 | 0% | 0.75% |
| Microparticles of Reference Example | 0% | 1.59% |

The invention claimed is:

1. A pharmaceutical composition for extended release comprising microparticles comprising a polymer matrix comprising a linear and a branched polylactide-o-glycolide polymer and pasireotide pamoate as an active ingredient produced by suspending pasireotide pamoate in a polymer solution, wherein said polymer solution comprises methylene chloride and a polymer mixture of said linear and said branched polylactide-co-glycolide polymer, wherein the concentration of the polymer mixture in methylene chloride is 15.9% weight of polymer per weight of polymer solution, preparing an aqueous solution comprising a stabilizer, mixing the suspended pasireotide pamoate in polymer solution with the stabilizer solution, evaporating off the methylene chloride, and filtering off the microparticles.

2. A process of making microparticles comprising—dissolving a mixture of a linear polylactide-co-glycolide polymer and a branched polylactide-co-glycolide polymer in methylene chloride to form a polymer solution wherein the concentration of the polymer mixture in methylene chloride is about 15.9 wt. % by weight of the polymer solution,
adding the polymer solution to pasireotide pamoate to form a polymer solution comprising pasireotide pamoate,
preparing an aqueous dispersion containing a stabilizer,
mixing the polymer solution comprising pasireotide pamoate with the aqueous dispersion containing the stabilizer,
evaporating the methylene chloride and filtering off the microparticles.

* * * * *